United States Patent
Hausmanns et al.

(10) Patent No.: US 7,374,780 B2
(45) Date of Patent: May 20, 2008

(54) TWO PART HARD SHELL CAPSULE MADE OF POLY(1,4-α-D-GLUCAN) AND STARCH

(75) Inventors: Stephan Hausmanns, Wiesbaden (DE); Wolfgang Luppe, Ladenburg (DE)

(73) Assignee: Sudzucker Aktiengesellschaft Mannheim/Ochsenfurt, Mannheim (DE)

( * ) Notice: Subject to any disclaimer, the term of this patent is extended or adjusted under 35 U.S.C. 154(b) by 571 days.

(21) Appl. No.: 10/478,796

(22) PCT Filed: May 31, 2002

(86) PCT No.: PCT/EP02/05949

§ 371 (c)(1),
(2), (4) Date: Nov. 25, 2003

(87) PCT Pub. No.: WO02/102355

PCT Pub. Date: Dec. 27, 2002

(65) Prior Publication Data

US 2004/0234761 A1    Nov. 25, 2004

(30) Foreign Application Priority Data

Jun. 1, 2001  (EP) .................................. 01113347

(51) Int. Cl.
*A61K 9/48* (2006.01)
(52) U.S. Cl. ...................................... 424/451; 424/453
(58) Field of Classification Search .................... None
See application file for complete search history.

(56) References Cited

U.S. PATENT DOCUMENTS

| 4,026,986 A | 5/1977 | Christen et al. |
| 4,738,724 A * | 4/1988 | Wittwer et al. .......... 106/206.1 |
| 6,323,265 B1 * | 11/2001 | Bengs et al. .................. 524/56 |

FOREIGN PATENT DOCUMENTS

| GB | 2 007 245 A | 5/1979 |
| WO | WO 92/09274 | 6/1992 |
| WO | WO 99/02600 | 1/1999 |
| WO | WO 9902600 A1 * | 1/1999 |
| WO | WO 01/37817 A1 | 5/2001 |

* cited by examiner

*Primary Examiner*—S. Tran
(74) *Attorney, Agent, or Firm*—Hamilton, Brook, Smith & Reynolds, P.C.

(57) ABSTRACT

The present invention relates to hard shell capsules consisting of two parts made from a poly(1,4-α-D-glucan)and starch based composition and the manufacturing thereof, preferentially by a dipping and pin molding process.

14 Claims, No Drawings

TWO PART HARD SHELL CAPSULE MADE OF POLY(1,4-α-D-GLUCAN) AND STARCH

RELATED APPLICATIONS

This application is the U.S. National Phase of International Application No. PCT/EP02/05949, filed 31 May 2002, published in English, which application claims priority under 35 U.S.C. § 119 or 365 to European Application No. 01113347.7, filed 1 Jun. 2001. The entire teachings of the above applications are incorporated herein by reference.

Two part hard shell capsule consisting essentially of poly(1,4-α-D-glucan) and starch.

The present invention relates to hard shell capsules consisting of two parts made from a poly(1,4-α-D-glucan) and starch based composition and the manufacturing thereof, preferentially by a dipping and pin moulding process.

Today, to produce satisfactory hard shell capsules gelatine and/or collagen, mostly in connection with plasticisers, are being used. Processes for there manufacture as well as such capsules themselves are disclosed in e.g. U.S. Pat. No. 1,787,777; U.S. Pat. No. 3,032,700; U.S. Pat. No. 3,802,272; U.S. Pat. No. 4,026,986; U.S. Pat. No. 4,196,564; U.S. Pat. No. 4,250,007; U.S. Pat. No. 4,268,265; U.S. Pat. No. 4,576,284; U.S. Pat. No. 4,738,817, Nduele et al., "The use of cassava starch in hard gelatine capsule formulations." J. Pharm. Belg. (1993), 48(5), pp 325-34, WO 96/10996 and U.S. Pat. No. 4,780,316.

These two part hard shell capsules are mainly being processed in solution and melt moulding processes. Since gelatine and collagen are of animal origin and their consumption gives raise to hygienic and ethical concerns, in particular with respect to animal diseases like BSE (Bovine Spongioforme Encephalopathy), nowadays products made from gelatine and/or collagen meet widespread rejection from customers, and it is up to now not clear whether there is a risk to sicken with BSE after consumption of such products.

Medicinal starch capsules consisting of two parts produced by a backing process from starch foam in a waffle mould were in use in the first part of the 20th century. These starch capsules were filled with the active ingredient manually and are of insufficient mechanical resistance to be used in modern filling automates.

Injection moulded two part starch capsules were disclosed e.g. in U.S. Pat. No. 4,738,818; U.S. Pat. No. 4,738,724; U.S. Pat. No. 4,539,060; and U.S. Pat. No. 4,591,475. The capsules obtained in this way were substantially consisting of amorphous starch whereupon brittleness occurred and the capsules were not resistant to impact and deformation in high performance filling units.

For the reasons above there have been many attempts in the art to develop other hard shell capsules consisting of material from non animal origin with satisfactory properties, at least with respect to mechanical strength. In JP 202003 capsules made of hemicellulose, carboxyrmethylcellulose or native starch, which are polysaccharides of the type poly(β-D-glucan) or poly(α-D-glucan), respectively, are disclosed. In WO 00/18835 capsules consisting essentially of starch ethers and oxydized starch are disclosed, whereas WO 96/10996 describes capsules based on I(iota)-carragenan. Water soluble cellulose derivatives for the manufacture of hard shell capsules in a dip moulding process have been further suggested e.g. in U.S. Pat. No. 5,698,155 and U.S. Pat. No. 5,431,917. These substances are rather expensive, and therefore this possibility is not generally accepted by capsule consumers. However, in spite of the so many attempts, none have succeeded in manufacturing cellulose capsules or other capsules of non-animal origin in large quantities with sufficient uniformity to be suitable for filling in modern high-speed filling machines.

Thus, in the art no fully satisfactory hard shell capsules consisting of non-animal material have been described nor are they available.

In view of the aforementioned facts there exists a high need in the art to develop new hard shell capsules consisting essentially of material from non-animal origin as an excipient, these new capsules being superior to capsules consisting essentially of material from non-animal origin already developed in the art at least with respect to mechanical strength.

Thus, it was one object of the present invention to provide hard shell capsules made from non-animal material, which should be highly resistant to impact and deformation in order to be applicable in state of the art high performance filling equipment, convenient for medicinal and cosmetic purposes, and these capsules should be superposable and tenable for prolonged periods of time.

Further objects of the present invention not explicitly mentioned here can easily be derived from the aforementioned facts.

The solution to the above mentioned objects of the present invention is achieved by providing the embodiments as characterised in the claims.

In one embodiment the present invention relates to two part hard shell capsules consisting essentially of a composition comprising (a) at least 1% per weight poly(1,4-α-D-glucan) (based on the total carbohydrat contents of the present composition), and (b) at the utmost 99% per weight starch (based on the total carbohydrat contents of the present composition), preferably chemically modified starch, and (c) between 1 to 60% per weight based on the total carbohydrat contents of the present composition of a plasticiser, wherein the poly(1,4-α-D-glucan) is characterised in that:
(i) the molar ratio of branched (1-4,-6)- and unbranched (1-4)-anhydroglucan units is $\leq 1 \times 10^{-3}$,
(ii) the number average degree of polymerisation $D(p)N$ lies in the range between 40 and 300, and
(iii) the weight fraction of cristallinity $f_{cystalline}$ is $\geq 0.35$.

and wherein the starch is characterised in
(iv) the number average degree of polymerisation $D(p)N$ is $\geq 1 \times 10^2$, and
(v) the molar ratio of branched (1-4,-6)- and unbranched (1-4)-anhydroglucan units is $\geq 0.2 \times 10^{-2}$, and wherein the resulting $Q_{branch}$ of the composition after mixing of (a) and (b) is $\geq 1 \times 10^{-5}$.

Preferably, the present composition consists of 5-50% per weight, based on the carbohydrat-contents of the present composition, poly(1,4-α-D-glucan), more preferably 10-40%, mostly preferably 10-30%.

Preferably, the present composition consists of 50-95% per weight, based on the carbohydrat-contents of the present composition, starch, more preferably 60-90%, mostly preferably 70-90%.

Poly(1,4-α-D-glucan) is a polymer of α-D-anhydroglucan units coupled by α-1,4 semiacetalic bonds. The chemical structure of the described polymer is a linear molecule in which the D-anhydroglucan units are coupled by α-1,4 bonds between the carbon atom (1) and the carbon atom (4) of the neighbouring anhydroglucan units.

From starch, poly(1,4-α-D-glucan)-structures with a certain degree of 1-6 branching of anhydroglucan units are well known in the art, resulting in slightly branched molecules (amylose and amylopectin, respectively, with branching degrees from about >$10^{-3}$ (amylose) up to $3 \times 10^{-2}$-$7 \times 10^{-2}$ (amylopectin)).

For the purposes of the present invention, branched units are designated "(1-4,-6) anhydroglucan units", unbranched units are designated "(1-4) anhydroglucan units".

Surprisingly the inventors found during the excessive experimentation that lead to the present invention that it is an essential feature of the poly(1,4-α-D-glucan) useful in the present invention that the molar ratio of the (1-4,6) anhydroglucan units and the (1-4) anhydroglucan units is limited.

It is assumed by the inventors that this is necessary to allow for a sufficient occurrence of linear chain segments in the molecule, which could possibly play a role in recrystallization processes, but this remains unclear.

For the purposes of the present invention, the molar ratio between (1-4,-6) anhydroglucan units and (1-4) anhydroglucan units is designated $Q_{branch}$.

According to the present invention, the upper limiting value for $Q_{branch}$ of the poly(1,4-α-D-glucan) is preferably $1 \times 10^{-3}$, that is to say the poly(1,4-α-D-glucan) molecules usable in the present invention range from molecules with $Q_{branch}$ of $1 \times 10^{-3}$ to molecules which are strictly linear ($Q_{branch}=0$). More preferably the upper limiting value is $1.5 \times 10^{-4}$, and an even more preferred upper limiting value is $1.5 \times 10^{-5}$, and it is mostly preferred when the upper limiting value is $1.5 \times 10^{-6}$.

It has been found that in the composition of the present invention, strictly linear poly(1,4-α-D-glucan) molecules are best suited to arrive at fully satisfactory hard shell capsules. On the other band, it was found that a slight degree of branching (up to $1 \times 10^{-3}$) may be tolerable in order to arrive at hard shell capsules with sufficient mechanical strength.

$Q_{branch}$ is measured as described in: Hitzukuri, S.: "Starch: Analytical Aspects in Carbohydrates", in Food, ed. by Eliasson, A.-Ch., Marcel Decker Inc. NY, Basel, Hong Kong, 1996.

It was further found that the poly(1,4-α-D-glucan) useful in the present invention preferably has a number average degree of polymerisation D(p)N of at least 40, preferably this value lies in a range from 40 to 300 and more preferably in a range between 50-100.

The number average degree of polymerisation is defined as:

$$D(p)N = \Sigma n_i \times Dp_i / \Sigma n_i$$

wherein:
$n_i$=number of molecules with a given degree of polymerisation
$Dp_i$=given degree of polymerisation
$_i$=serial index D(p)N is measured by GPC and MALDI-TOF, as described by C. Koch, "Methods for studying starch characteristics" PhD-Thesis 1999, Department of Food Science, Swedish University of Agricultural Science, Uppsala, No. Agraria 163.

Furthermore it has been found that the cristallinity of the poly(1,4-α-glucan) usable in the present invention is correlated besides others with the linearity of the molecule ($Q_{branch}$) and the respective D(p)N of the molecule.

To be able to compare the crystallinity of different samples the following standardised crystallisation process is used:

In a confined volume 5 g of the poly(1,4-α-D-glucan) sample is dissolved in 95 water at 137° C. and the solution is kept at this temperature for 3 minutes. The solution is than cooled to 22° C. and kept for 48 hours at this temperature at 30% humidity. The resulting dry substance is characterised by wide angle x-ray diffraction.

Methods to measure the cristallinity of a probe of polysaccharides can be found in Frech, D, J. Jpn. Soc. Starch, 1972 19,8 and Zobel, H. F., Starch/Stärke 1988, 40, 1.

The resulting distribution of the intensity in arbitrary units as a function of the scattering angle is integrated between the limits of integration 5 to 35 degrees scattering angle and designated as $I_{total}$.

The same procedure is done for the intensity distribution of the scattering by the crystallites and designated as $I_{crystalline}$.

The quotient $I_{crystalline}/I_{total}=f_{crystalline}$ is the crystalline fraction or cristallinity of the sample.

It has been found that the cristallinity ($f_{cristalline}$) of the poly(1,4-α-D-glucan) usable in the present invention should be at least 0.35. More preferably, the value is $\geq 0.4$ and a most preferred value is $\geq 0.45$.

As long as the aforementioned range of $Q_{branch}$ and the aforementioned D(p)N as well as the mentioned $f_{crystalline}$ are applied, any poly(1,4-α-D-glucan) from any given source may be used according to the invention.

Furthermore it has been found that the composition of the present invention is specially well suited for the intended purpose, if the resulting $Q_{branch}$ after mixing together components (a) and (b) is equal to or above $1 \times 10^{-5}$, a preferred value is equal to or above $1 \times 10^{-4}$, it is more preferred when this value is equal to or above $1 \times 10^{-4}$, and it is mostly preferred when this value is equal to or above b $1 \times 10^{-2}$.

In a preferred embodiment of the present invention the poly(1,4-α-D-glucan) is produced by an enzymatic method using the enzyme amylosucrase disclosed in WO 95/31553.

In a further preferred embodiment of the present invention, the poly(1,4-α-D-glucan) usable in the present invention is made from native starches, e.g. by enzymatic and/or chemical debranching methods well known in the art.

Furthermore, the poly(1,4-α-D-glucan) usable in the present invention may be obtained from animal sources like glycogen.

The poly(1,4-α-D-glucan) may as well be obtained from sources like e.g. bacteria, fungi or algae, which have been genetically modified in order to produce the above poly(1,4-α-D-glucan)s with low $Q_{branch}$ values or which are strictly linear.

The poly(1,4-α-D-glucan) usable in the present invention may be chemically modified. These modifications can be accomplished e.g. by esterification, etherification or selective oxidation in 2-, 3- or 6-Position.

For the purposes of the present invention, the term "modification" means that any free hydroxyl group of the poly(1,4-α-D-glucan) can be used to introduce new chemical entities. In principle any modification described in greater detail later on in the context of the starch component of the present composition may be applied to the poly(1,4-α-D-glucan) as well.

Unmodified poly(1,4-α-D-glucan) is preferred.

The above described poly(1,4-α-D-glucan) shows a remarkably pronounced tendency to generate structures with regular conformation, e.g. double helices and shows a high degree of cristallinity, what can be shown by X-ray diffraction and 13 C nuclear magnetic resonance.

It is assumed by the authors that due to this tendency the above poly(1,4-α-D-glucan) is specially well suited as an essential ingredient of the composition according to the present invention.

As a result of the above defined characteristics of the preferred poly(1,4-α-D-glucan), specially with respect to $D(p)N$ and $Q_{branch}$ this polyglucan shows a pronounced tendency to be water-insoluble.

The water insolubility of the poly(1,4-α-D-glucan) used according to the invention is expediently such that at least 98%, in particular at least 99.5% of the poly(1,4-α-D-glucan) used are water-insoluble under standard conditions (T=25° C., p=101325 Pascal ), in accordance with classes 4-7 of the German Pharmacopae DAB, Wissenschaftliche Verlagsbuchhandlung mbH, Stuttgart, Govi-Verlag GmbH, Frankfurt, $9^{th}$ edition 1987).

These classes correspond to the categories sparingly soluble, slightly soluble, very slightly soluble and practically insoluble.

In addition to other advantages of the two part hard shell capsule of the invention, the inventors found that by using such an water-insoluble poly(1,4-α-D-glucan) as part of the composition used to produce said capsule, one can easily produce hard shell capsules with remarkably decreased tendency of water-immigration/-sorption and with reduced hygroscopicity, which results in an improved shelf life and durability of the ready-made product, e.g. capsule plus active ingredient.

For example, the hygroscopicity of the ready-made product, e.g. the capsule of the present invention, may be determined by measuring the increase in weight of the capsule over the time in an atmosphere with defined water concentration. These methods are very well known to those skilled in the art.

The occurrence of such an advantageous effect was surprising, since it is sufficient if only the poly(1,4-α-D-glucan) portion of the composition is water-insoluble, whereas the other, starch-part of the composition is not.

Therefore, it is preferred that the poly(1,4-α-D-glucan) used according to the invention belongs to classes 4-7 of the DAB. It is more preferred if the poly(1,4-α-D-glucan) belongs to classes 5-7 of the DAB. Even more preferred the poly(1,4-α-D-glucan) belongs to classes 6-7 of the DAB.

The other main component of the composition of the invention is starch, either native or chemically modified.

Starches preferably useful in the present invention have a number average degree of polymerisation $D(p)N \geq 10^2$ and the respective $Q_{branch}$ is $\geq 1 \times 10^{-6}$, preferably $\geq 1 \times 10^{-4}$ and mostly preferred $\geq 2 \times 10^{-3}$.

Therefore, the starches preferably usable in the present invention can easily be distinguished from the poly(1,4-α-D-glucan) which forms the other main component of the composition of the present invention, since the poly(1,4-α-D-glucan) usable in the present invention has a $Q_{branch} \leq 10^{-3}$.

According to the present invention, any starch can be used as long as the above $D(p)N>10^2$ and $Q_{branch} \geq 2 \times 10^{-3}$ is applied. Also mixtures of different types of starches can be applied. Examples of starches which can be used according to the present invention comprise, inter alia, starch from tubers, such as potatoes, cassava, tapioca, maranta, sweet potato, from seeds such as wheat, corn, rye, rice, barley, millet, oats, sorghum, from fruits such as chestnuts, acorns, beans, peas and other legumes, banana and from plant piths, e.g. of the sago palm.

The starches usable in the present invention consist essentially of amylose and amylopectin in varying ratios.

According to the present invention, the term "modified starch" means any starch which was altered in order to change their properties or behaviour under different circumstances. The modifications introduced comprise altering the amylose/amylopectin ratio, gelatinization prior to use, partial hydrolytic or enzyme-based degradation or introduction of new chemical entities.

Specially, modified starches are starches with newly introduced chemical groups, e.g. dialdehyde-starches, carboxy-starches, hydroxypropylated starches or native starches with introduced cationic and/or anionic side groups. Chemically modified starches are well known in the art.

The modification thus is mainly achieved by reactions on the polymer, in which starch is treated with mono- or polyfunctional reagents or oxidizing agents. This preferably entails the hydroxyl groups of the polyglucans of the starch being. converted by esterification, etherification or selective oxidation. Another possibility consists of graft copolymerization, initiated by free radicals, of copolymerizable unsaturated monomers onto the starch backbone.

Particular chemically modified starches include, inter alia, starch esters such as xanthates, acetates, phosphates, sulfates, nitrates, starch ethers such as, e.g., non-ionic, anionic or cationic starch ethers, oxidized It was found that in order to produce hard shell capsules from the above mentioned composition, it is necessary that at least 1% per weight of the resulting composition is represented by the poly(1,4-α-D-glucan). An upper limiting value is 99% per weight.

The same applies for the starch component of the present invention.

As long as the above values are maintained, the composition of the present invention can be used to produce hard shell capsules with improved properties. It was found by the authors of the present invention that the resulting composition is specially well suited for the production of hard shell capsules, if the resulting mean value $Q_{branch(total)}$ of the composition of the invention after mixing the poly(1,4-α-D-glucan) and the starch component, respectively, is equal or above $2 \times 10^{-3}$.

A third essential component of the composition of the present invention is a plasticiser. The plasticiser can be chosen from the group consisting of water; polyalcohols as e.g. ethylene glycol, glycerol, propanediol, erythriol, mannitol, sorbitol; multivalent aliphatic carbonic acids as e.g. maleic acid, succinic acid; multivalent hydroxyaliphatic carbonic acids as e.g. lactic acid, 2-hydroxybutanoic acid, citric acid, malic acid; dimethyl sulfoxide, urea or other starch-solvents.

Of this group, preferred plasticisers are water and glycerol. Specially preferred is water.

Although a plasticiser is needed in order to work the present invention, the nature of the plasticiser is not as important as the above described components (a) and (b) of the composition of the present invention. On the other hand, as the hard shell capsules of the present invention are mainly intended for medicinal and cosmetic use, i. e. for oral administration, it is clear to one skilled in the art of making capsules, that this plasticiser should be per se edible, i.e. non toxic. Therefore, any edible, non-toxic solvent for starch known in the art may be used as a plasticiser according to the invention. For the same reasons, water is the preferred plasticiser according to the invention.

For one skilled in the art it becomes clear that mixtures of plasticisers may be used without leaving the scope of the invention.

Besides the aforementioned essential components (a), (b) and (c) the composition of the present invention may further comprise additives, e.g. lubricants, fillers and flavouring substances. These additives may be added depending on the intended use of the capsule. The respective additives are well known in the art, and there is no need to list them here.

Surprisingly the inventors found that mixtures of poly(1,4-α-D-glucan) synthesised by the enzyme amylosucrase from sucrose in vitro as disclosed in WO 95/31553 and starch, preferably modified starch, give layers of high mechanical flexibility and strength on coating and drying from their aqueous solutions.

Films shaped to capsules from mixtures comprising poly(1,4-α-D-glucan) and modified starch were prepared with high throughput filling equipment normally used to make hard gelatine capsules consisting of two parts by a pin dipping and moulding process.

It was further found that the mechanical properties of the films can be improved by additives, e.g. fillers and lubricants.

Recrystallisation of the poly(1,4-α-D-glucan) and starch composition takes place during cooling and drying of the solution coated on the pin mould in the capsule forming process. It is assumed by the inventors that due to the fast recrystallisation (circa 10-20 seconds) of the composition of the present invention consisting essentially of poly(1,4-α-D-glucan) and starch coated on the pins in the pin moulding process an aqueous gel is formed, stabilising the coated layer and allowing the movement of air in the drying section of the moulding machine. In the absence of an elastic gel phase the movement of the drying air would deform the coated aqueous layer. The fast formation of the elastic gel phase of the aqueous solution of poly(1,4-α-D-glucan) and starch allows stable layer formation and stabilisation during the drying process.

This may be an explanation for the surprising fact that compositions with at least a certain degree of the above defined poly(1,4-α-D-glucan) and starch are able to build films that are sufficiently stable in order to be used to produce the hard shell capsules of the present invention, since it is assumed that the fast recristallization is depending on the linear or at least showing only a very little degree of branching and rather small (small Dp(N)) poly(1,4-α-D-glucan) molecules usable in the present invention.

The dip moulding machine usable in the present invention consists of a container for solutions of the capsule shell material, pin bars carrying the pin shaped mould, the mechanism transporting the pin bars in the machine, hoods with inlets and outlets for air with controlled humidity (the humidity of air at temperature T is expressed in weight % of the humidity of air saturated with water vapour at temperature T) and temperature. Devices to cut off the open edge of the capsule shells on the pin mould and the release of the capsule shells from the mould. This machine is described in detail in U.S. Pat. No. 1,787,777. In the conventional hard shell capsule process aqueous solution of gelatine and additives is placed into the container and the pins are coated with a lubricant and set to a selected temperature. The transport mechanism for the mould bars enters the pins directed downwards into the gelatine solution and removes them after selected duration for the coating. The pin bars are then rotated by even integers for the number of half rotations resulting upwards oriented pins on the bars which are transported into the space covered by the first hood. Circulation of air is maintained around the pins coated with the gelatine solution. The pin bars are continuously transported into the space covered by further hoods. The temperature and level of the gelatine solution in the container, the humidity and temperature in the hoods and the speed of transport of the pin bars are controlled. The open end of the capsule shell is cut off on the pin and the shells are released from the pins. The mould bars are then cleaned in an automatic process and reintroduced into the mould process.

In the present invention the specifications for the solutions, temperatures, air humidity and speeds of transport are adapted to the composition containing poly(1,4-α-D-glucan) and starch replacing the gelatine in the aqueous solution placed into the container of the capsule making machine:

Weight fraction of the poly(1,4-α-D-glucan) in the applied aqueous solution is in the range 0.01-0.7, preferentially is in the range 0.05-0.5, more preferentially is in the range 0.1-0.2.

Poly(1,4-α-D-glucan) and starch are dissolved in water and additives at temperatures T1 in the range $50 < T1 < 180°$ C., preferentially in the range $50 < T1 < 100°$ C.

The aqueous solution of the poly(1,4-α-D-glucan) and starch composition is kept in the container at controlled values of temperature T2 in the range $50 < T2 < 95°$ C.

The temperature T3 and humidity h1 of the air circulating in the first hood in order to allow for controlled cooling of the aqueous solution coated on the pins of the pin dipping and moulding machine is kept at controlled values in the ranges $10 < T3 < 140°$ C. and $5 < h1 < 99\%$.

The temperature T4 and humidity h2 of the air circulating in the second hood in order to allow for controlled cooling of the aqueous solution coated on the pins of the pin dipping and moulding machine is kept at controlled values in the ranges $10 < T4 < 135°$ C. and $5 < h2 < 95\%$.

The temperature T5 and humidity h3 of the air circulating in the third hood in order to allow for controlled cooling of the aqueous solution coated on the pins of the pin dipping and moulding machine is kept at controlled values in the ranges $10 < T5 < 130°$ C. and $5 < h3 < 90\%$.

The temperature T6 and humidity h4 of the air circulating in the fourth hood in order to allow for controlled cooling of the aqueous solution coated on the pins of the pin dipping and moulding machine is kept at controlled values in the ranges $10 < T6 < 125°$ C. and $5 < h4 < 85\%$.

The temperature T7 and humidity h5 of the air circulating in the fifth hood in order to allow for controlled cooling of the aqueous solution coated on the pins of the pin dipping and moulding machine is kept at controlled values in the ranges $10 < T6 < 120°$ C. and $5 < h4 < 80\%$.

Transport of the pin bars through the machine is set to speeds to achieve for the duration of coating in lasts 0.1 to 30 seconds, preferentially 1 to 10 seconds;

duration of the rotation lasts 0.1 to 10 seconds, preferentially 1 to 3 seconds;

duration for the cooling of the pin bars in the five hoods lasts 5 to 50 minutes, preferentially 20 to 40 minutes.

The poly(1,4-α-D-glucan) based composition may further comprise other polysaccharides, polyesters, fats, proteins and derivatives thereof, preferentially of plant, microbiological or biotechnological origin, which optionally may be further modified by e.g. hydrolysis and/or reduction, respectively. It is preferred that the amount of water in the capsule shell made from the aforementioned composition varies in the range of 0.005 to 0.2% per weight, more preferred 0.02 to 0.1% per weight corresponding to the thermodynamic equilibrium with the surrounding atmosphere.

In said water content range the capsules may be kept for several years without damage. The capsules consist of an upper cover part and a lower part to accommodate the active ingredients, and they are mechanically resistant to impact and deformation in widespread used high performance capsule filling equipment. The capsules made from the composition of the invention show an increased barrier effect against additional water immigration or atmospheric gas transfer and disintegrate under physiological conditions within short time to release the encapsulated material.

The capsules may be used to any encapsulation purpose, and they are specially suited for pharmaceutical and/or cosmetic and/or food, food additive or food supplement or food ingredient purposes.

Furthermore, the capsules are especially well suited for encapsulation of fragrances or colorants/dyes, e.g. in the form of paintballs.

To illustrate the invention the following non-limiting examples and comparative examples are provided.

As comparative examples native starches with amylose content <70% per weight and water soluble chemically substituted starches made therefrom were dissolved in water and used in the dip moulding process according to the present invention. These resulted in a film with insufficient mechanical resistance towards forces generated during the manufacturing steps of the dip moulding process: drying and mould releasing. The resulting films were brittle on deformation. The same insufficient properties were observed when the two part capsules are made in an injection moulding process, no matter if the applied composition contains poly(1,4-α-D-glucan) or not.

EXAMPLE 1

Poly(1,4-α-D-glucan) characterised by $Q_{branch} < 10^{-6}$, $f_{crystalline} = 0.45$ and D(p)N=80, and potato starch (about 80% amylopectin) was used to produce capsules. 10% per weight poly(1,4-α-D-glucan) was combined with 90% per weight Amyloplast PE 004. To 1 kg of this composition 0.2 kg of plasticiser containing glycerol, sorbitol and other sugar alcohols prepared by reduction of sugars was added and dissolved with 8.8 kg water at 140° C. in confined volume. The solution of poly(1,4-α-D-glucan), starch and plasticiser was kept at 90° C. for 2 hours and transferred to the container in a dip moulding machine. Temperature of the container for the starch solution was 90° C. The dip moulding machine to produce the capsule shells was equipped with pin bars carrying ten pins of length 20 cm and diameter 4 cm. The transport of the pin bars was selected to give 30 minutes for the coating, drying, cutting and mould release. The coated pins were transported through 5 hoods with temperatures of drying air 65, 40, 25, 20 and 15° C.; the humidity of the drying air were 60, 50, 30, 20 and 10%. The resulting capsules were cut into strips and the elongation and stress at brake was determined (see table 1).

EXAMPLE 2

5% per weight of the poly(1,4-α-D-glucan) of example 1 was combined with 95% per weight of the potato starch and this composition was used in this example in the otherwise same procedure as in example 1. The mechanical properties of the produced films are given in table 1.

EXAMPLE 3

15% per weight of the poly(1,4-α-D-glucan) of example 1 was combined with 85% per weight of the potato starch and this composition was used in this example in the otherwise same procedure as in example 1. The mechanical properties of the produced films are given in table 1.

COMPARATIVE EXAMPLE 1

The potato starch was replaced by poly(1,4-α-D-glucan) of example 1 in the otherwise same procedure as in example 1. The mechanical properties of the produced films are given in table 1.

COMPARATIVE EXAMPLE 2

The poly(1,4-α-D-glucan) of example 1 was replaced by the potato starch in this example in the otherwise same procedure as in example 1. The mechanical properties of the produced films are given in table 1.

TABLE 1

Results of examples 1-3 and comparative examples 1-2

| No. of example | $f_{cristalline}$ | $Q_{branch}$** | D(p)N | stress [MPA] at brake of film samples | strain of capsule shell |
|---|---|---|---|---|---|
| Example 1 | n.d. | $0.9 \times 10^{-2}$ | 3800 | 30 | 1.5 |
| Example 2 | n.d. | $0.95 \times 10^{-2}$ | 3900 | 20 | 1.2 |
| Example 3 | n.d. | $0.85 \times 10^{-2}$ | 3700 | 50 | 1.7 |
| Comparative Example 1 | 0.45 | 0 | 80 | * | * |
| Comparative Example 2 | 0.02 | $10^{-2}$ | 4000 | <1 | <1.05 |

*no layer could be produced
**after mixing together components (a) and (b), e.g. poly(1,4-α-D-glucan) and starch The results of examples 1 to 3 show that a combination of poly(1,4-α-D-glucan) and potato starch (Amyloplast™) results in films useful in the applied process for making hard shell two part capsules. The results of the comparative examples 1 and 2 show that neither poly(1,4-α-D-glucan) nor Amyloplast alone result in useful films in the applied process for making hard shell two part capsules. Furthermore, the resulting mechanical properties of the dry layers of the capsule shells—their elongation at least 1.2 and stress at least 20 MPA at break—are fulfilling the recommendations for their applicability.

The invention claimed is:
1. Two part hard shell capsule, the shell consisting essentially of:
   (a) at least 1% per weight poly(1,4-α-D-glucan), based on the total carbohydrate content of the composition, and
   (b) at the utmost 99% per weight starch, based on the total carbohydrate content of the composition, together with
   (c) between 1 to 60% per weight of a plasticiser, based on the total carbohydrate content of the composition,
   wherein the poly(1,4-α-D-glucan) (a) is characterised in:
   (i) the molar ratio of branched (1-4,-6)- and unbranched (1-4)-anhydroglucan units is $<1 \times 10^{-3}$,
   (ii) the number average degree of polymerisation D(p)N lies in the range between 40 and 300, and
   (iii) the weight fraction of cristallinity $f_{crystalline}$ is greater than 0.35,
   and wherein the starch (b) is characterised in

(iv) the number average degree of polymerisation $D(p)N$ is $>10^2$, and
(v) the molar ratio of branched (1-4,-6)- and unbranched (1-4)-anhydroglucan units is greater than $0.2\times10^{-2}$,
and wherein
(vi) the resulting $Q_{branch}$ of the composition after mixing of (a) and (b) is greater than or equal to $1\times10^{-5}$.

2. Two part hard shell capsule according to claim 1, the resulting $Q_{branch}$ (vi) of the composition after mixing of (a) and (b) being greater than or equal to $0.2\times10^{-2}$.

3. Two part hard shell capsule according to claim 1, the molar ratio of item (i) of branched (1-4,-6)-and unbranched (1-4)-anhydroglucan units is less than $1.5\times10^{-4}$.

4. Two part hard shell capsule according to claim 1, the $Dp(N)$ of item (ii) being from 50 to 100.

5. Two part hard shell capsule according to claim 1, the $f_{crystalline}$ of item (iii) being greater than or equal to 0.4.

6. Two part hard shell capsule according to claim 1, the starch fraction (b) being 50-90% per weight, based on the carbohydrate-contents of the composition.

7. Pin dipping and moulding process for the production of a two part hard shell capsule according claim 1.

8. Two part hard shell capsule according to claim 1 containing a food additive, a food supplement or a food ingredient.

9. Two part hard shell capsule according to claim 1 containing a pharmaceutically active ingredient.

10. The two-part hard shell capsule of claim 1, wherein the starch fraction (b) is chemically modified starch.

11. The two part hard shell capsule of claim 1, wherein the molar ratio of item (i) of branched (1-4,-6)- and unbranched (1-4)-anhydroglucan units is less than $1,5\times10^{-5}$.

12. The two part hard shell capsule of claim 1, wherein the $f_{crystalline}$ of item (iii) is greater than or equal to 0.45.

13. The two part hard shell capsule of claim 1, wherein the starch fraction (b) is 60-90% per weight, based on the carbohydrate-contents of the composition.

14. The two part hard shell capsule of claim 1, wherein the starch fraction (b) is 70-90% per weight, based on the carbohydrate-contents of the composition.

* * * * *